United States Patent
Mariani (10) Patent No.: US 10,136,881 B2
(45) Date of Patent: Nov. 27, 2018

(54) LAPAROSCOPIC RETRACTOR DEVICES

(71) Applicant: Mayo Foundation for Medical Education and Research, Rochester, MN (US)

(72) Inventor: Andrea Mariani, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 648 days.

(21) Appl. No.: 14/614,616

(22) Filed: Feb. 5, 2015

(65) Prior Publication Data

US 2015/0223795 A1    Aug. 13, 2015

Related U.S. Application Data

(60) Provisional application No. 61/938,234, filed on Feb. 11, 2014.

(51) Int. Cl.
*A61B 1/32* (2006.01)
*A61B 17/02* (2006.01)

(52) U.S. Cl.
CPC ................ *A61B 17/0218* (2013.01)

(58) Field of Classification Search
CPC combination set(s) only.
See application file for complete search history.

(56) References Cited

U.S. PATENT DOCUMENTS

| | | | |
|---|---|---|---|
| 5,178,133 A | 1/1993 | Pena | |
| 5,267,554 A | 12/1993 | Wilk | |
| 5,271,385 A | 12/1993 | Bailey | |
| 5,353,784 A * | 10/1994 | Nady-Mohamed | A61B 17/0218 600/205 |
| 5,439,476 A | 8/1995 | Frantzides | |
| 5,441,044 A | 8/1995 | Tovey et al. | |
| 6,913,610 B2 | 7/2005 | Nakao | |
| 7,052,502 B2 | 5/2006 | Le Huec | |
| 7,112,172 B2 | 9/2006 | Orban et al. | |
| 7,122,003 B2 | 10/2006 | Nakao | |

(Continued)

FOREIGN PATENT DOCUMENTS

| EP | 2088934 | 8/2009 |
|---|---|---|
| EP | 3075322 | 10/2016 |

(Continued)

OTHER PUBLICATIONS

"Comparison of EZ Surgical A-LapTM and Diamond Flex Retractor," Eisner USA.com [online] modified Nov. 1, 2010. Retrieved from the Internet: <URL: http://www.eisnerusa.com/download/comparison/Comparison+Table_A+Lap+Diamond+Flex+retractor.pdf, 2 pages.

(Continued)

*Primary Examiner* — Sameh Boles
(74) *Attorney, Agent, or Firm* — Fish & Richardson P.C.

(57) ABSTRACT

Devices for performing medical procedures such as laparoscopic surgery are provided herein. For example, this document provides laparoscopic retractor devices. In some embodiments, the laparoscopic retractor devices provided herein include two retractor blades that can be expanded or contracted. Further, in some embodiments an elastic covering is included, and the retractor blades are disposed within the elastic covering.

17 Claims, 7 Drawing Sheets

(56) References Cited

U.S. PATENT DOCUMENTS

| | | | |
|---|---|---|---|
| 7,766,823 | B2 | 8/2010 | Moll et al. |
| 8,007,508 | B2 | 8/2011 | Cox |
| 8,097,008 | B2 | 1/2012 | Henderson |
| 8,562,522 | B2 | 10/2013 | Antanaitis |
| 8,840,638 | B2 | 9/2014 | Sherwinter |
| 9,107,648 | B2 | 8/2015 | Ransden et al. |
| 9,314,153 | B2 | 4/2016 | Stein et al. |
| 9,326,757 | B2 | 5/2016 | Ravikumar et al. |
| 9,445,800 | B2 | 9/2016 | Nguyen |
| 2003/0225432 | A1 | 12/2003 | Baptiste et al. |
| 2005/0043750 | A1 | 2/2005 | Scott, III et al. |
| 2007/0213595 | A1 | 9/2007 | Ravikumar |
| 2008/0146881 | A1 | 6/2008 | Alimi et al. |
| 2009/0192360 | A1 | 7/2009 | Riess et al. |
| 2010/0174149 | A1 | 7/2010 | Moll et al. |
| 2010/0228093 | A1 | 9/2010 | Voegele et al. |
| 2010/0292718 | A1 | 11/2010 | Sholev et al. |
| 2011/0082479 | A1* | 4/2011 | Friedlander ........... A61F 2/0063 606/151 |
| 2011/0105848 | A1 | 5/2011 | Sadovsky et al. |
| 2011/0144450 | A1 | 6/2011 | Paolitto et al. |
| 2012/0046525 | A1 | 2/2012 | Russell et al. |
| 2012/0059225 | A1 | 3/2012 | Gostout et al. |
| 2012/0088978 | A1 | 4/2012 | Park et al. |
| 2012/0123215 | A1 | 5/2012 | Begg |
| 2012/0238824 | A1 | 9/2012 | Widenhouse et al. |
| 2012/0245417 | A1 | 9/2012 | Winterberg et al. |
| 2013/0066155 | A1 | 3/2013 | Keating et al. |
| 2013/0172682 | A1 | 7/2013 | Ransden et al. |
| 2014/0039264 | A1 | 2/2014 | Heiman |
| 2014/0316209 | A1 | 10/2014 | Overes et al. |
| 2015/0065805 | A1 | 3/2015 | Edmondson et al. |
| 2015/0245828 | A1 | 9/2015 | Harari et al. |
| 2016/0256147 | A1 | 9/2016 | Jeong et al. |
| 2016/0278756 | A1 | 9/2016 | Aho et al. |

FOREIGN PATENT DOCUMENTS

| | | |
|---|---|---|
| GB | 245990 | 11/2009 |
| WO | WO2008068405 | 6/2008 |
| WO | WO 2010094799 | 8/2010 |

OTHER PUBLICATIONS

"iLap: A New Laparoscopic Retractor," 2011 [retrieved on Sep. 11, 2015]. Retrieved from the Internet: <URL: http://blogs.ucc.ie/wordpress/biodesign/biodesign-2011/>, 4 pages.

"UZit A-Lap™," ezsurgical.com [online], archived Aug. 29, 2014 [retrieved on Sep. 23, 2015]. Retrieved from the Internet: <URL: https://web.archive.org/web/20140829004856/http://ezsurgical.com/Products.asp?Page=UZit>, 2 pages.

Alimi et al., "Intestinal retractor for transperitoneal laparoscopic aortoiliac reconstruction: experimental study on human cadavers and initial clinical experience," Surg Endosc., 14(10):915-919, Oct. 2000.

Autosutre, "Endo Retract™ II 10 mm Retractor," Bio-Medicine.org [online] archived Sep. 2, 2014. Retrieved from the Internet: <URL: https://web.archive.org/web/20140902102146/http://www.bio-medicine.org/medicine-products/ENDO-RETRACT-26trade-3B-II-10-mm-Retractor-11126-1/>.

Autosuture, "Endo Mini-Retract™ 5 mm Retractor," Bio-Medicine.org [online] archived Jan 15, 2009. Retrieved from the Internet: <URL: https://web.archive.org/web/20090115091133/http://www.bio-medicine.org/medicine-products/ENDO-MINI-RETRACT-26trade-3B-5-mm-Retractor-11124-1/>, 1 page.

Autosuture, "Endo Paddle Retract™ 12 mm Retractor," Bio-Medicine.org [online] archived Nov. 26, 2014. Retrieved from the Internet: <URL: https://web.archive.org/web/20141126231117/http://bio-medicine.org/medicine-products/ENDO-PADDLE-RETRACT-26trade-3B-12-mm-Retractor-11122-1/>, 1 page.

Autosuture, "Endo Peanut™ 5 mm Retractor," Bio-Medicine.org [online] archived Dec. 3, 2008. Retrieved from the Internet: <URL:https://web.archive.org/web/20081203114049/http://www.bio-medicine.org/medicine-products/ENDO-PEANUT-26trade-3B-5-mm-Retractor-11121-1/>, 1 page.

Autosuture, "Endo Retract™ 10 mm Retractor," bio-medicine.org [online] archived Dec. 3, 2008. Retrieved from the Internet: <URL:https://web.archive.org/web/20081203113738/http://www.bio-medicine.org/medicine-products/ENDO-RETRACT-26trade-3B-10-mm-Retractor-11125-1/>, 1 page.

Autosuture, "Endo Retract™ Maxi 10 mm Retractor," Bio-Medicine.org [online] archived Dec. 3, 2008. Retrieved from the Internet: <URL: https://web.archive.org/web/20081203113912/http://www.bio-medicine.org/medicine-products/ENDO-RETRACT-26trade-3B-Maxi-10-mm-Retractor-11123-1/>, 1 page.

Autosuture, "Extrahand™ Balloon Retractor," Bio-Medicine.org [online] archived Sep. 2, 2014, Retrieved from the Internet: <URL: https ://web.archive.org/web/20140902110631/http://www.bio-medicine.org/medicine-products/EXTRAHAND-26trade-3B-Balloon-Retractor-11131-1/>, 1 page.

Barbera et al., "Newly designed retraction devices for intestine control during laparoscopic aortic surgery: a comparative study in an animal model," Surg Endosc., 14(1):63-66, Jan. 2000.

CareFusion, "Snowden-Pencer® laparoscopic articulating retractors," Carefusion.com [online] 2012 [retrieved on Sep. 14, 2015]. Retrieved from the Internet: <http://www.carefusion.com/pdf/Surgical_Instrumentation/Articulating_retractors_brochure.pdf>, 4 pages.

Gyms ACMI, "Soft-Wand™ Balloon Retractor," [product catalog] 2 pages, 2008.

Paolucci et al., "Exposure of the operative field in laparoscopic surgery," Surg Endosc., 11(8):856-863, Aug. 1997.

* cited by examiner

LAPAROSCOPIC RETRACTOR DEVICES

CROSS-REFERENCE TO RELATED APPLICATIONS

This application claims the benefit of U.S. Provisional Application Ser. No. 61/938,234, filed Feb. 11, 2014. The disclosure of the prior application is considered part of (and is incorporated by reference in) the disclosure of this application.

BACKGROUND

1. Technical Field

This document relates to devices for performing medical procedures such as laparoscopic surgery. For example, this document relates to retractor devices such as laparoscopic bowel retractors for use in performing intra-abdominal surgery.

2. Background Information

Optimal visualization of the operative field is a fundamental principle in surgery. Any technique that improves intra-operative visualization has the potential to make surgery safer and more cost efficient. With the advent of minimally invasive surgery, the utilization of laparoscopic or robotic surgery is becoming the standard of care for many abdominal surgeries. However, there are areas of the abdominal cavity, like the paraaortic area, in which the minimally invasive approach is still challenging. In fact, small bowel loops frequently obscure the paraaortic surgical field, especially in obese patients.

Endometrial cancer is the fourth most prevalent malignancy in the United States. It is estimated that approximately 40% of endometrial cancer patients need to have a paraaortic lymphadenectomy, which involves surgery in the area of the aorta and vena cava. In 70% of such cases, the surgical site is either partially or completely obstructed by the small bowel, making the procedure sometimes impractical to perform by minimally invasive robotic surgery.

Some intestinal retraction devices are either too small for the amount of bowel that needs to be restrained, too cumbersome to use, or too difficult to retrieve. There is a need for an improved bowel retractor device that is convenient to operate and effective for keeping the bowel away from the operative field, including for obese patients.

SUMMARY

This document provides devices for performing medical procedures such as laparoscopic surgery. For example, this document provides laparoscopic retractor devices. In some embodiments, the laparoscopic retractor devices provided herein include two retractor blades that can be expanded or contracted. Further, in some embodiments an elastic covering is included, and the retractor blades are disposed within the elastic covering.

In general, one aspect of this document features a laparoscopic retractor device. The laparoscopic retractor device comprises a handle and an elongate shaft with a proximal end portion that is attached to the handle. The shaft extends from the handle and terminates at a distal free end portion. The shaft includes a first lumen therethrough. The laparoscopic retractor device further comprises an elongate shaft linkage disposed within the first lumen. The shaft linkage has a proximal end and a distal end. The laparoscopic retractor device further comprises an actuator located at the handle and coupled to the proximal end of the shaft linkage, and an expandable portion coupled to the shaft at the distal free end portion and coupled to the distal end of the shaft linkage. In some embodiments, moving the actuator causes the expandable portion to move radially outward from the shaft or radially inward toward the shaft.

Some implementations of the laparoscopic retractor device may further comprise an elastic covering that is disposed around the expandable portion. In various implementations of the laparoscopic retractor device the actuator may be slidable in relation to the handle. In some implementations, sliding the actuator distally may cause the expandable portion to expand, and sliding the actuator proximally may cause the expandable portion to contract. The expandable portion may comprise at least two retractor blades in some embodiments. In some such embodiments, causing the expandable portion to expand may comprise causing the at least two retractor blades to move radially outward from the shaft, and causing the expandable portion to contract may comprise causing the at least two retractor blades to move radially inward toward the shaft. Further, in some implementations the at least two retractor blades may be elongate blades that include axes that are substantially parallel to a longitudinal axis of the shaft and remain substantially parallel to the axis of the shaft while moving radially outward from and inward toward the shaft. Still further, in some implementations the expandable portion may further comprise scissor arms, and the scissor arms may be pivotably coupled to the at least two retractor blades and to the shaft. Some such implementations may further comprise an elastic covering that may be disposed around the at least two retractor blades.

In another general aspect, this document features another laparoscopic retractor device embodiment comprising: a handle; an elongate shaft with a proximal end portion that is attached to the handle, the shaft extending from the handle and terminating at a distal free end portion, the shaft including a first lumen therethrough; an elongate shaft linkage disposed within the first lumen, the shaft linkage having a proximal end and a distal end; a first actuator located at the handle and coupled to the proximal end of the shaft linkage; an expandable portion coupled to the shaft at the distal free end portion and coupled to the distal end of the shaft linkage, wherein moving the actuator causes the expandable portion to move radially outward from the shaft or radially inward toward the shaft; and a sheath with a lumen therethrough, at least a portion of the shaft being disposed within the lumen, the sheath being slidable distally and proximally along the shaft.

Some implementations of the laparoscopic retractor device may further comprise an elastic covering that is disposed around the expandable portion of the another laparoscopic retractor device embodiment. In various implementations of the laparoscopic retractor device embodiment the sheath may include a hub that is connected to a proximal end of the sheath, and the hub may include an second actuator whereby the hub can be locked and unlocked from being coupled to the shaft. In some embodiments, the first actuator may be slidable in relation to the handle. In particular embodiments, sliding the first actuator distally may cause the expandable portion to expand, and sliding the first actuator proximally may cause the expandable portion to contract. Optionally, the expandable portion may comprise at least two retractor blades. In some implementations, causing the expandable portion to expand may comprise causing the at least two retractor blades to bend and to move radially outward from the shaft, and causing the expandable portion to contract may comprise causing the at least two retractor blades unbend and to move radially inward toward the shaft. In particular implementations, by sliding the sheath distally at least some portion of the at least two retractor blades can be made to move further radially away from the shaft. Further, by sliding the sheath proximally at least some portion of the at least two retractor blades can be made to move further radially inward toward the shaft in some implementations. The laparoscopic retractor device may further comprise an elastic covering that is disposed around the at least two retractor blades.

Particular embodiments of the subject matter described in this document can be implemented to realize one or more of the following advantages. In some embodiments, the laparoscopic retractor devices provided herein are readily adjustable in size from a low profile contracted configuration to a substantially wider expanded configuration for performing retraction of tissue and organs. The laparoscopic retractor devices provided herein have intuitive and easy to operate designs. In some embodiments, various surgeries can be performed in a minimally invasive fashion using the devices and methods provided herein. Such minimally invasive techniques can reduce recovery times, patient discomfort, and treatment costs. In some embodiments, the laparoscopic retractor devices provided herein are designed to minimize the risk of pinching or impinging tissue during the adjustment of the retractors between the contracted and expanded configurations. Further, the laparoscopic retractor devices provided herein do not include separable pieces. As such, clinicians can operate the retractor devices without a risk of pieces becoming detached within a body cavity.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described herein. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description herein. Other features, objects, and advantages of the invention will be apparent from the description and drawings, and from the claims.

DESCRIPTION OF THE DRAWINGS

Like reference numbers represent corresponding parts throughout.

DETAILED DESCRIPTION

This document provides devices for performing medical procedures such as laparoscopic surgery. For example, this document provides laparoscopic retractor devices. In some embodiments, the laparoscopic retractor devices provided herein include two retractor blades that can be expanded or contracted. Further, in some embodiments an elastic covering is included, and the retractor blades are disposed within the elastic covering.

In one example implementation, the laparoscopic retractor devices provided herein can be used for performing surgeries such as, but not limited to, paraaortic lymphadenectomy procedures to treat endometrial cancer. Also, the laparoscopic bowel retractors provided herein may help to gain exposure and visualization of the surgical field in other areas of the abdomen that are obscured by the bowel, including other types of laparoscopic or robotic surgeries. In addition to such intra-abdominal surgeries, in some cases the laparoscopic bowel retractor devices provided herein may be used for procedures in other medical specialties such as, but not limited to, urology, vascular surgery, and general surgery.

Figure 1A:
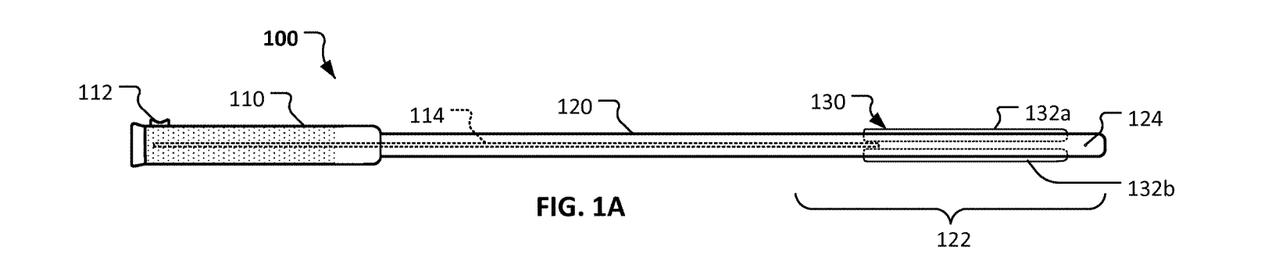
FIG. 1A is a side view of a laparoscopic bowel retractor device, shown in a contracted configuration, in accordance with some embodiments provided herein.

Referring to FIG. 1A, an example laparoscopic retractor device 100 in accordance with some embodiments provided herein includes a handle 110, a shaft 120, and an expandable portion 130. The proximal end of shaft 120 is fixedly coupled to handle 110. As will be explained further below, expandable portion 130 is movably coupled to shaft 120 at a distal end portion 122 of shaft 120 where shaft 120 terminates with a free end. It should be understood that the figures included in this disclosure are not necessarily to scale. However, the figures appropriately depict the design concepts so as to facilitate one of ordinary skill in the art to practice the inventive laparoscopic bowel retractor devices provided herein.

Laparoscopic retractor device 100 is shown in a contracted configuration. This contracted configuration may be used, for example, when inserting distal portion 122 of laparoscopic retractor device 100 into an internal space such as an abdomen of a patient, and thereafter when withdrawing laparoscopic retractor device 100. In some implementations, distal portion 122 of laparoscopic retractor device 100 is inserted into a patient, while a proximal portion of laparoscopic retractor device 100 remains external to the patient.

In some circumstances, a trocar device is utilized as a portal to provide access to the patient's internal space such as the abdominal space. In such cases, distal portion 122 of laparoscopic retractor device 100 can be passed through the trocar. In some such cases, a trocar with an inner diameter of about 1 centimeter (cm) is used, and distal portion 122 of laparoscopic retractor device 100 can be passed therethrough when distal portion 122 is in the contracted configuration. In other implementations, laparoscopic retractor device 100 can be used with trocars having other inner diameter sizes, such as about 0.7 cm, about 0.8 cm, about, 0.9 cm, about 1.1 cm, about 1.2 cm, about 1.3 cm, about 1.4 cm, about 1.5 cm, about 1.6 cm, about 1.7 cm, about 1.8 cm, about 1.9 cm, or about 2.0 cm. Laparoscopic retractor device 100 can be provided in a range of sizes (diameters and lengths), and the suitably sized laparoscopic retractor device 100 can be selected for use in such various implementations. It should be understood that the use of a trocar may not be required in some implementations. In some other implementations, laparoscopic retractor device 100 can be passed through an incision.

Laparoscopic retractor device 100 includes shaft 120. In some embodiments, shaft 120 is comprised of a metallic material. For example, metallic materials including, but not limited to, stainless steels (e.g., austenitic 316 stainless steel or martensitic 440 and 420 stainless steels), titanium, titanium alloys (e.g., Ti6Al4V), and the like, can be used for shaft 120. In other embodiments, shaft 120 can be comprised of a polymeric material. For example, polymeric materials including, but limited to, polyvinyl chloride (PVC), PEBEX, PICOFLEX, TECOFLEX, PTFE, ePTFE, FEP, PEEK, silicone, urethane, polyethylene, polypropylene, and the like, can be used for shaft 120. In some embodiments, at least portions of shaft 120 can be malleable or articulable.

As will be explained further below, shaft 120 includes at least one lumen. A shaft linkage 114 that extends from handle 110 to expandable portion 130 runs through the lumen and is slidable therein. In some embodiments, shaft linkage 114 is a solid metallic rod (e.g., stainless steel), or a solid polymeric rod (e.g., TEFLON, DELRIN, polyurethane, and the like). In other embodiments, a Bowden cable is used for shaft linkage 114.

In some embodiments, shaft 120 includes more than one lumen. For example, one or more additional lumens can be optionally included in shaft 120 for purposes such as, but not limited to, suction, irrigation, and the like. In some cases, the optional lumen(s) has a diameter of about 5 millimeters (mm), but other smaller or larger sized lumens can be included in some embodiments.

Figure 1B:
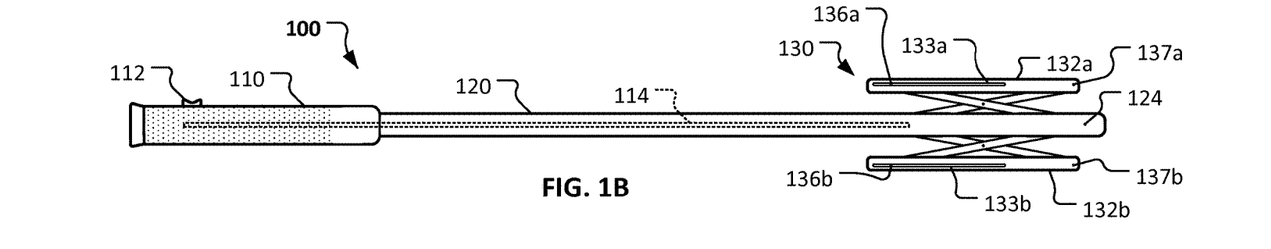
FIG. 1B is a side view of the laparoscopic retractor device of FIG. 1A shown in a partially expanded configuration.
Figure 1C:
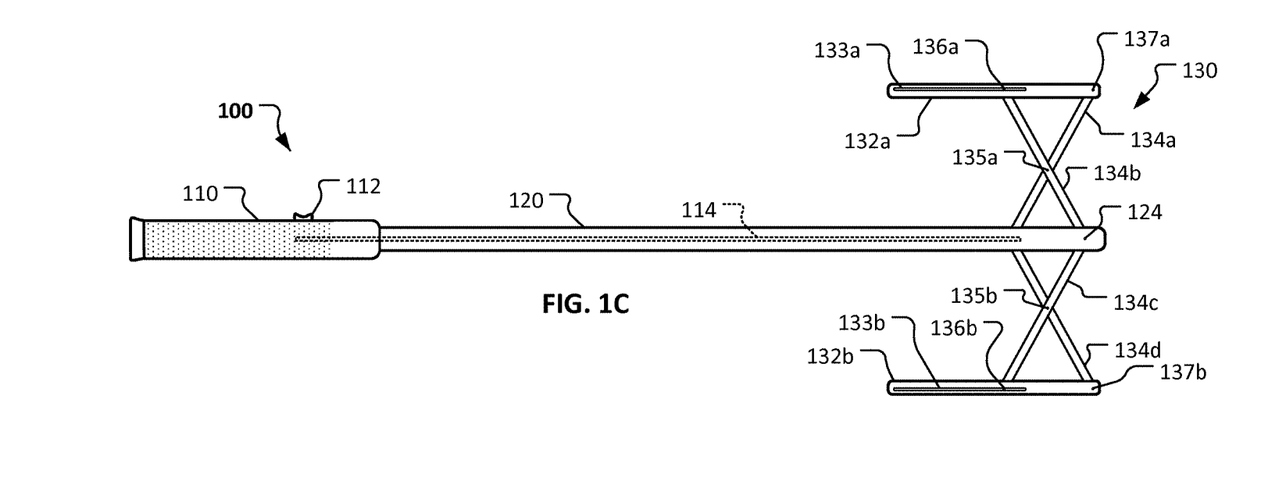
FIG. 1C is a side view of the laparoscopic retractor device of FIG. 1A shown in an expanded configuration.

Referring now to FIGS. 1A-1C, distal portion 122 of laparoscopic retractor device 100 can be expanded in situ (e.g., after insertion of laparoscopic retractor device 100 into the patient) to facilitate the retraction of internal tissue, such as the patient's intestines in the case of an intra-abdominal implementation. Such expansion of distal portion 122 is depicted in FIGS. 1B (partial expansion) and 1C (nearly full expansion).

Laparoscopic retractor device 100 also includes handle 110. Handle 110 can be comprised of any suitable metallic or polymeric material such as, but not limited to, polymethyl methacrylate, polystyrene, acrylonitrile butadiene styrene (ABS), PVC, polyethylene, polypropylene, polycarbonate, and the like. Handle 110 can include a textured or contoured surface so that a clinician can get a good grip on handle 110.

Handle 110 includes a sliding actuator knob 112. Sliding actuator knob 112 can be used by an operator of laparoscopic retractor device 100 to expand or retract expandable portion 130. That is, in some embodiments sliding actuator knob 112 can be depressed and slid distally or proximally in relation to handle 110. Such sliding of sliding actuator knob 112 can expand or retract expandable portion 130 because of shaft linkage 114 that is connected therebetween. Sliding actuator knob 112 can lock in place on the handle when the operator is no longer depressing sliding actuator knob 112. In other embodiments, other types of actuators can be used as alternatives to sliding actuator knob 112. For example, a rotary actuator, a level, a trigger, and other types of actuators can be used in some embodiments.

Laparoscopic retractor device 100 also includes expandable portion 130. Expandable portion 130 includes retractor blades 132a and 132b that are movably coupled to shaft 120 and shaft linkage 114 via scissor arms 134a, 134b, 134c, and 134d. Using such a mechanical arrangement, retractor blades 132a and 132b can be moved radially inward and outward from shaft 120 while remaining essentially parallel to shaft 120.

One end of scissor arm 134a is pivotably coupled to retractor blade 132a using a pin 137a. The other end of scissor arm 134a is pivotably coupled to shaft linkage 114.

One end of scissor arm 134b is pivotably coupled to retractor blade 132a using a pin 136a that can translate in a slot 133a located in retractor blade 132a. The other end of scissor arm 134b is pivotably coupled to shaft 120 using a pin 124.

One end of scissor arm 134c is pivotably coupled to retractor blade 132b using a pin 137b. The other end of scissor arm 134c is pivotably coupled to shaft linkage 114.

One end of scissor arm 134d is pivotably coupled to retractor blade 132b using a pin 136b that can translate in a slot 133b located in retractor blade 132b. The other end of scissor arm 134d is pivotably coupled to shaft 120 using a pin 124.

Scissor arms 134a and 134b are pivotably coupled together near their midpoints using a pin 135a. Similarly, scissor arms 134c and 134d are pivotably coupled together near their midpoints using a pin 135b.

The components of expandable portion 130 can be metallic or polymeric. For example, in some embodiments some or all of the components of expandable portion 130 can be metals such as, but not limited to, stainless steels, titanium, titanium alloys, NiTi, and the like. In some embodiments, some or all of the components of expandable portion 130 can be polymers such as, but not limited to, DELRIN, TEFLON, polyurethane, polyethylene, polypropylene, and the like. In some embodiments, a combination of metallic and polymeric materials can be used to construct expandable portion 130.

In some embodiments, retractor blades 132a and 132b are double-sided. In some such embodiments, retractor blades 132a and 132b have a U-shaped cross-section (like a channel) and the ends of scissor arms 134a-b are within the channels (or between the double-sided retractor blades 132a and 132b).

Figure 2A:
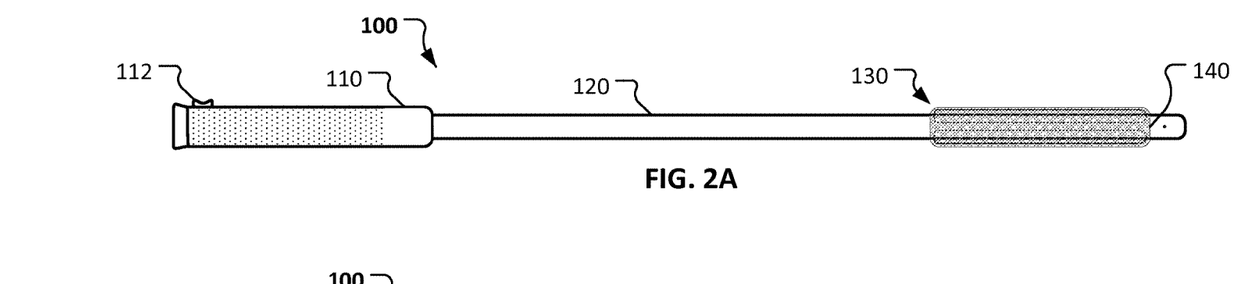
FIGS. 2A-2C show the laparoscopic retractor device of FIG. 1A in the same configurations of FIGS. 1A-1C, and with the addition of an example elastic covering on the expandable portion, in accordance with some embodiments provided herein.
Figure 2B:
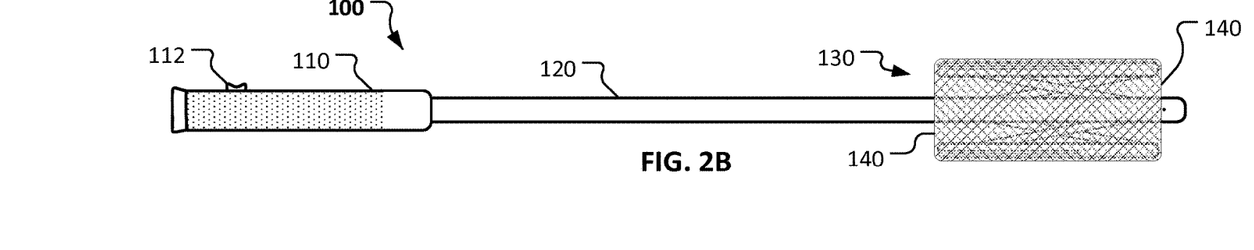
Figure 2C:
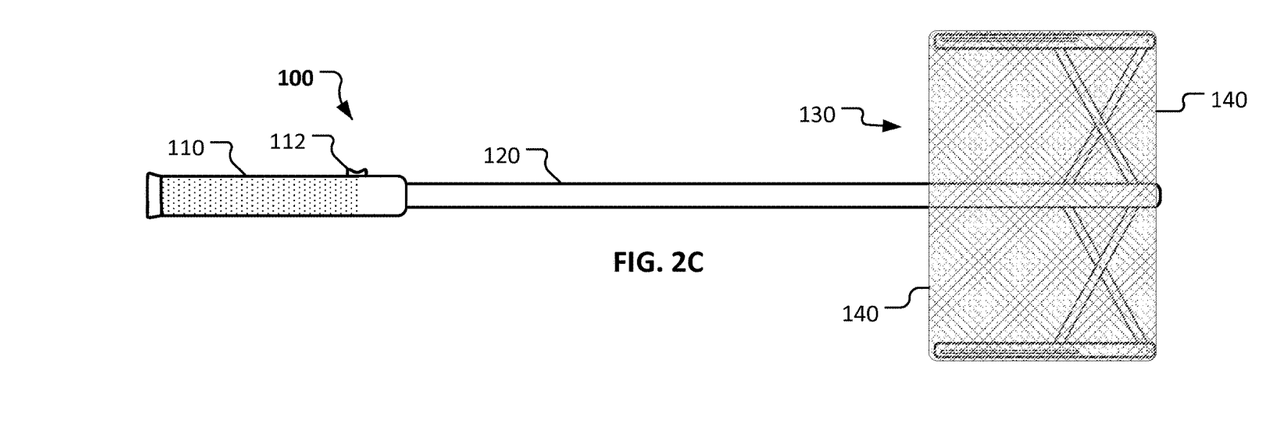

Referring now to FIGS. 2A-2C, laparoscopic retractor device 100 can include an elastic covering 140 on expandable portion 130. Elastic covering 140 can be a sleeve of stretchable material that surrounds and conforms to retractor blades 132a and 132b.

When retractor blades 132a and 132b are in the contracted configuration as shown in FIG. 2A, elastic covering 140 is also contracted such that it snugly conforms to retractor blades 132a and 132b. As retractor blades 132a and 132b are expanded radially outward from shaft 120, elastic covering 140 stretches to remain surrounding and conforming to retractor blades 132a and 132b (as shown in FIGS. 2B and 2C). In some embodiments, elastic covering 140 is attached to retractor blades 132a and 132b, such as by using a biocompatible adhesive, clips, barbs, or another type of fastening means. In some embodiments, elastic covering 140 simply elastically surrounds retractor blades 132a and 132b.

Elastic covering 140 can be comprised of various materials. For example, in some embodiments elastic covering 140 can be made of materials including, but not limited to, polypropylene, natural latex, polyester, spandex, silicone, and the like. In some embodiments, elastic covering 140 can comprise nitinol. In some embodiments, a combination of such materials can be used to make elastic covering 140. The materials used to make elastic covering 140 can be knitted, woven, spun, extruded, molded, and the like. In some embodiments, elastic covering 140 is a mesh or netting type of material. In some embodiments, elastic covering 140 is a fabric, sheet, membrane, film, or the like. In particular embodiments, elastic covering 140 can be porous or at least partially porous so as to let fluids pass through some or all portions of elastic covering 140.

Elastic covering 140 can provide functional benefits for laparoscopic retractor device 100 in some situations. For example, elastic covering 140 can enlarge the area that expandable portion 130 comprises. Accordingly, laparoscopic retractor device 100 with elastic covering 140 can provide additional retraction capabilities as compared to laparoscopic retractor device 100 without elastic covering 140, in some situations. Additionally, in some situations the use of elastic covering 140 can reduce the likelihood of pinching tissue such as bowels when laparoscopic retractor device 100 with elastic covering 140 is being expanded or retracted, as compared to laparoscopic retractor device 100 without elastic covering 140.

Figure 3A:
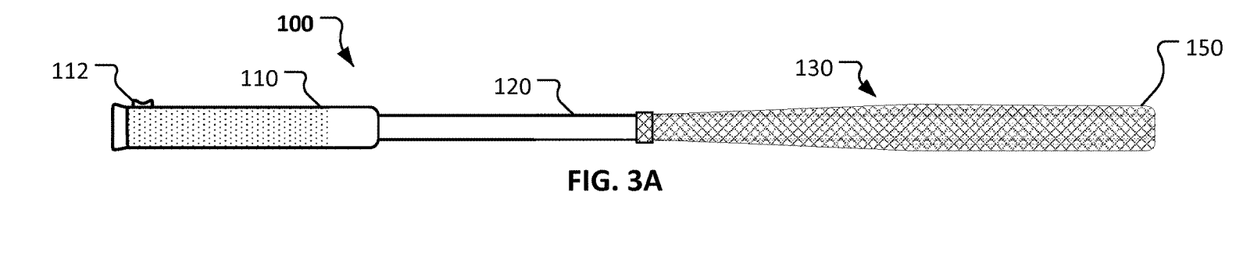
FIGS. 3A-3C show the laparoscopic retractor device of FIG. 1A in the same configurations of FIGS. 1A-1C, and with the addition of another example elastic covering on the expandable portion, in accordance with some embodiments provided herein.
Figure 3B:
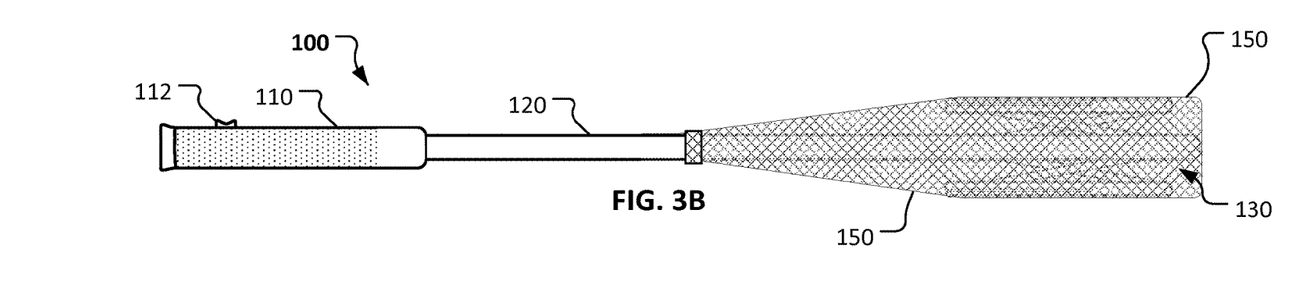
Figure 3C:
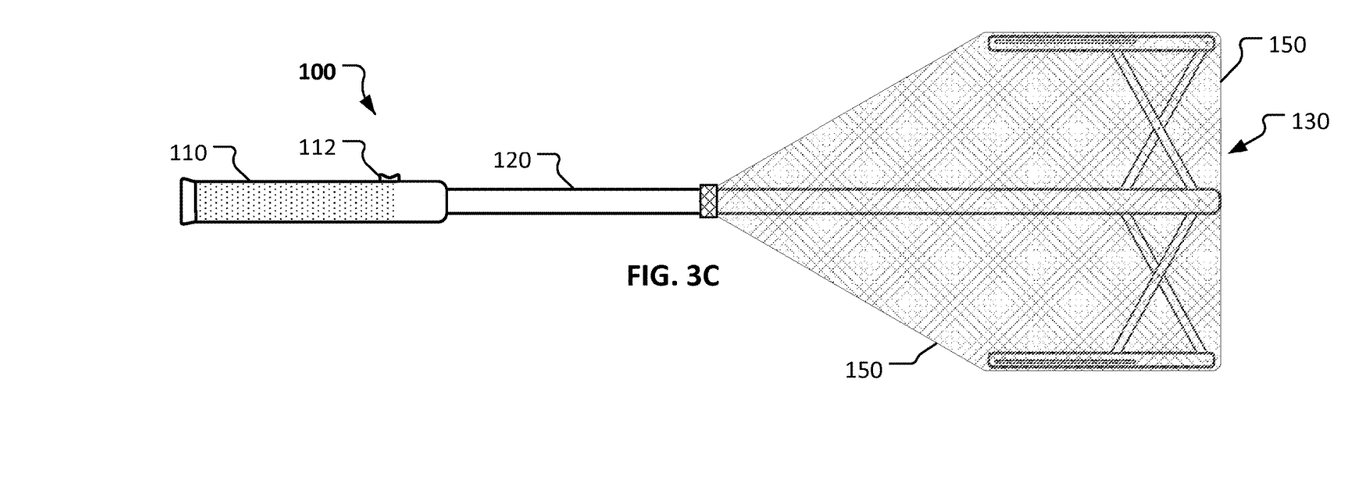

Referring now to FIGS. 3A-3C, some embodiments of laparoscopic retractor device 100 can include an elastic covering 150 of another type on expandable portion 130. Elastic covering 150 can be a sleeve of stretchable material that is attached to shaft 120 and that surrounds and conforms to retractor blades 132a and 132b.

When retractor blades 132a and 132b are in the contracted configuration as shown in FIG. 3A, elastic covering 150 is also contracted such that it snugly conforms to retractor blades 132a and 132b. As retractor blades 132a and 132b are expanded radially outward from shaft 120, elastic covering 150 stretches to remain surrounding and conforming to retractor blades 132a and 132b (as shown in FIGS. 3B and 3C). In some embodiments, elastic covering 150 is attached to retractor blades 132a and 132b, such as by using a biocompatible adhesive, clip, barbs, or another type of fastening means. In some embodiments, elastic covering 150 simply elastically surrounds retractor blades 132a and 132b.

Elastic covering 150 can be comprised of the same materials and made using the same construction techniques as elastic covering 140 described above. Additionally, the uses and advantages of elastic covering 150 are analogous to those of elastic covering 140 described above.

Figure 4A:
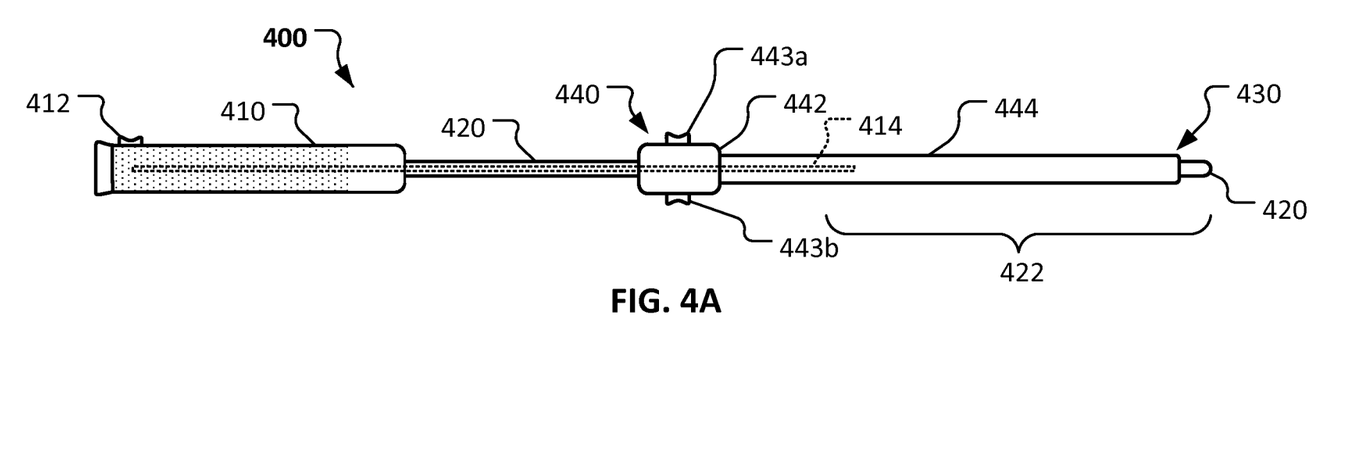
FIG. 4A is a side view of another laparoscopic bowel retractor device, shown in a contracted configuration, in accordance with some embodiments provided herein.

Referring now to FIG. 4A, another example laparoscopic retractor device 400 in accordance with some embodiments provided herein includes a handle 410, a shaft 420, an expandable portion 430, and a sheath 440. Expandable portion 430 is located at a distal end portion 422 of shaft 420 where shaft 420 terminates at a free end. The proximal end of shaft 420 is fixedly coupled to and extending from handle 410. Sheath 440 is slidably disposed over shaft 420 and expandable portion 430. As will be explained further below, a shaft linkage 414 is coupled to a sliding actuator knob 412 and to expandable portion 430.

Laparoscopic retractor device 400 is shown in a contracted configuration. This contracted configuration may be used, for example, when inserting distal portion 422 of laparoscopic retractor device 400 into an internal space of a patient, and when withdrawing laparoscopic retractor device 400. In some implementations, distal portion 422 of laparoscopic retractor device 400 is inserted into a patient, while a proximal portion of laparoscopic retractor device 400 remains external to the patient.

In some circumstances, a trocar device is utilized as a portal to provide access to an internal space of the patient, such as the patient's abdominal space. In such cases, distal portion 422 of laparoscopic retractor device 400 can be passed through the trocar. In some such cases, a trocar with an inner diameter of about 1 cm is used, and distal portion 422 of laparoscopic retractor device 400 can be passed therethrough. In other implementations, trocars with other inner diameter sizes are used (and the laparoscopic retractor device 400 can be passed therethrough), such as about 0.7 cm, about 0.8 cm, about, 0.9 cm, about 1.1 cm, about 1.2 cm, about 1.3 cm, about 1.4 cm, about 1.5 cm, about 1.6 cm, about 1.7 cm, about 1.8 cm, about 1.9 cm, or about 2.0 cm. Laparoscopic retractor device 400 can be provided in a range of sizes (diameters and lengths), and the suitably sized laparoscopic retractor device 400 can be selected for use in such various implementations. It should be understood that the use of a trocar may not be required in all implementations. In some other implementations, laparoscopic retractor device 400 can be passed through an incision.

Laparoscopic retractor device 400 includes shaft 420. Shaft 420 can be constructed of the same types of materials as shaft 120 described above. As will be explained further below, shaft 420 includes at least one lumen. Shaft linkage 414 extends from handle 410 to expandable portion 430, running through the lumen and being slidable therein. In some embodiments, shaft linkage 414 is a solid metallic rod (e.g., stainless steel), or a solid polymeric rod (e.g., TEFLON, DELRIN, polyurethane, and the like). In other embodiments, a Bowden cable is used for shaft linkage 414.

In some embodiments, shaft 420 includes more than one lumen. For example, one or more additional lumens can be optionally included in shaft 420 for purposes such as, but not limited to, suction, irrigation, and the like. In some cases, the optional lumen(s) has a diameter of about 5 mm, but other smaller or larger sized lumens can be included in some embodiments.

Laparoscopic retractor device 400 also includes sheath 440. Sheath 440 includes a hub 442, and a tube 444 that is attached to and extending from hub 442. Sheath 440 has a lumen within which at least a portion of shaft 420 and expandable portion 430 can be positioned, as desired, when sheath 440 is positioned at a distal location as shown in FIG. 4A. Sheath 440 can be slid proximally and distally along shaft 420 by a clinician operator. Hub 442 includes buttons 443a-b that can be depressed to unlock sheath 440 from shaft 420 such that sheath 440 can be slid along shaft 420. When buttons 443a-b are released, sheath 440 is locked to shaft 420. Accordingly, an operator can slide sheath 440 proximally or distally along shaft 420 and then release sheath 440 in a desired location, at which sheath 440 will stay. In other embodiments, buttons 443a-b can be replaced by other types of mechanisms that are lockable and releasable, such as an eccentric locking ring, a set screw or thumb screw, a friction fitting arrangement, a ratchet and pawl mechanism, a threaded arrangement, and the like.

In some embodiments, sheath 440 is comprised of a metallic material. For example, metallic materials including, but not limited to, stainless steels (e.g., austenitic 316 stainless steel or martensitic 440 and 420 stainless steels), titanium, titanium alloys (e.g., Ti6Al4V), and the like, can be used for sheath 440. In other embodiments, sheath 440 can be comprised of a polymeric material. For example, polymeric materials including, but limited to, polyvinyl chloride (PVC), PEBEX, PICOFLEX, TECOFLEX, PTFE, ePTFE, FEP, PEEK, silicone, urethane, polyethylene, polypropylene, and the like, can be used for sheath 440. In some embodiments, sheath 440 can be malleable.

Figure 4B:
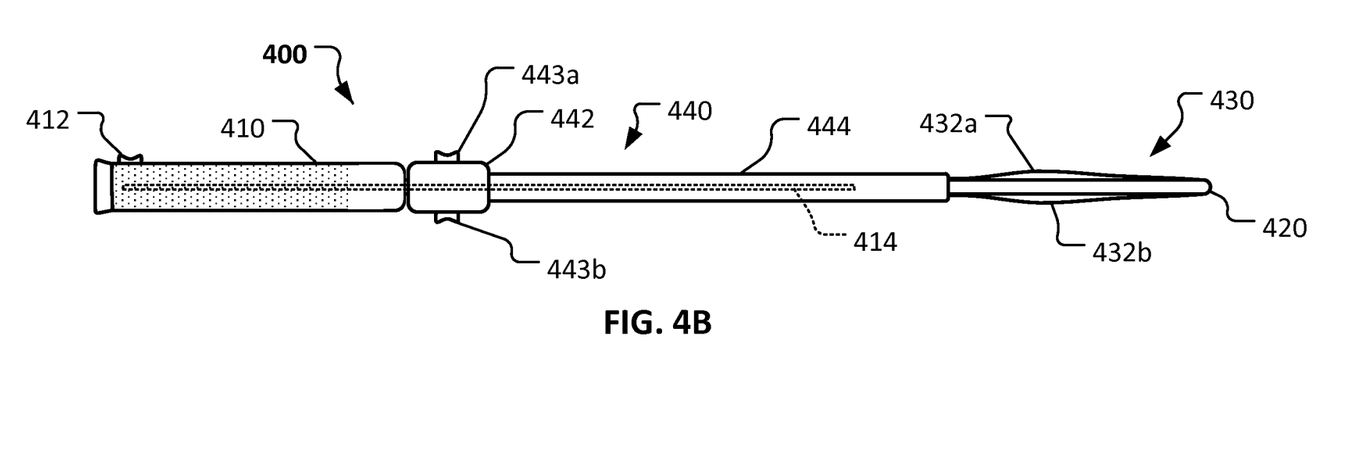
FIG. 4B is a side view of the laparoscopic retractor device of FIG. 4A showing a revealed expandable portion.

Referring now to FIGS. 4A-4D, distal portion 422 of laparoscopic retractor device 400 can be expanded in situ (e.g., after insertion of laparoscopic retractor device 400 into the patient) to facilitate the retraction of internal tissue, such as the patient's intestines in the case of an intra-abdominal implementation. Such expansion of distal portion 422 is depicted in FIGS. 4B (partial expansion), 4C (nearly full expansion), and 4D (full expansion).

Laparoscopic retractor device 400 also includes handle 410. Handle 410 can be comprised of any suitable polymeric material such as, but not limited to, polymethyl methacrylate, polystyrene, acrylonitrile butadiene styrene (ABS), PVC, polyethylene, polypropylene, polycarbonate, and the like. Handle 410 can include a textured or contoured surface so that a clinician can get a good grip on handle 410.

Handle 410 includes sliding actuator knob 412. Sliding actuator knob 412 can be used by an operator of laparoscopic retractor device 400 to expand or retract expandable portion 430. That is, in some embodiments sliding actuator knob 412 can be depressed and slid distally or proximally in relation to handle 410. Such sliding of sliding actuator knob 412 can expand or retract expandable portion 430 because of shaft linkage 414 therebetween. Sliding actuator knob 412 can lock in place on the handle when the operator is no longer depressing sliding actuator knob 412. In other embodiments, other types of actuators can be used as alternatives to sliding actuator knob 412. For example, a rotary actuator, a level, a trigger, and other types of actuators can be used in some embodiments.

Laparoscopic retractor device 400 also includes expandable portion 430. Expandable portion 430 includes retractor blades 432a and 432b that are movably coupled to shaft 420 and shaft linkage 414. Using such a mechanical arrangement, retractor blades 432a and 432b can be moved radially inward and outward from shaft 420 by moving sliding actuator knob 412 along handle 410.

The retractor blades 432a and 432b can be metallic or polymeric. For example, in some embodiments retractor blades 432a and 432b can be made of metals such as, but not limited to, stainless steels, titanium, titanium alloys, NiTi, and the like. In some embodiments, retractor blades 432a and 432b can be made of polymers such as, but not limited to, DELRIN, TEFLON, graphite, nylon, silicone, polyurethane, polyethylene, polypropylene, and the like. In some embodiments, a combination of metallic and polymeric materials can be used to construct retractor blades 432a and 432b.

Retractor blades 432a-b are slender, and very flexible and resilient in bending. Accordingly, retractor blades 432a-b can be moved radially outward from shaft 420 and radially inward toward shaft 420 by compressing and uncompressing retractor blades 432a-b by the linear action of shaft linkage 414.

In FIG. 4B, sheath 440 has been slid proximally so as to reveal expandable portion 430. Retractor blades 432a-b are visible but generally laying close to shaft 420 in a contracted configuration.

Figure 4C:
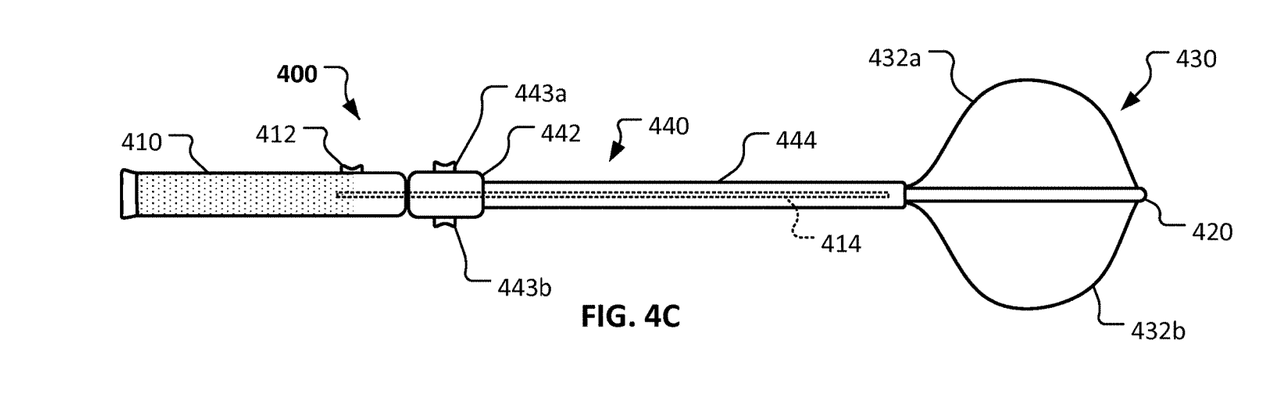
FIG. 4C is a side view of the laparoscopic retractor device of FIG. 4A shown in an expanded configuration.

In FIG. 4C, sliding actuator knob 412 has been slid distally along handle 410. Accordingly, shaft linkage 414 translates distally in coordination with movement of sliding actuator knob 412. The distal end of shaft linkage 414 being coupled to retractor blades 432a-b, as shaft linkage 414 translates distally retractor blades 432a-b become extended from shaft 420. In this expanded configuration, laparoscopic retractor device 440 can be used for retraction.

Figure 4D:
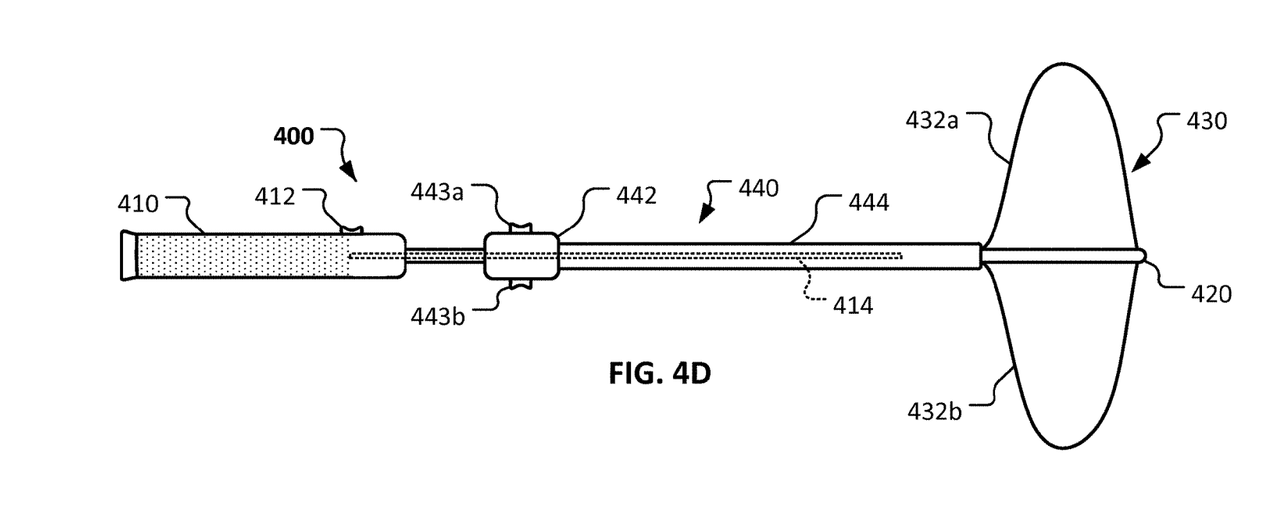
FIG. 4D is a side view of the laparoscopic retractor device of FIG. 4A shown in another expanded configuration.

In FIG. 4D, sheath 440 has been slid distally along shaft 420. Accordingly, retractor blades 432a-b are reshaped to a flatter but wider arrangement. During this step, sliding actuator knob 412 may also be moved further distally if so desired. In should be understood from the description herein, that an operator can configure retractor blades 432a-b in a variety of distinct shapes or configurations by moving sliding actuator knob 412 and sheath 440 in various positions to create the shape of retractor blades 432a-b as desired.

Retractor blades 432a-b can be expanded and retracted with little risk of impinging tissue, such as the bowels in the case of intra-abdominal use. This feature can be advantageous for patient safety and ease of use for laparoscopic retractor device 400.

Referring now to FIGS. 5A-5D, laparoscopic retractor device 400 can include an elastic covering 450 on expandable portion 430. Elastic covering 450 can be a sleeve of stretchable material that surrounds and conforms to retractor blades 432a and 432b.

Figure 5A:
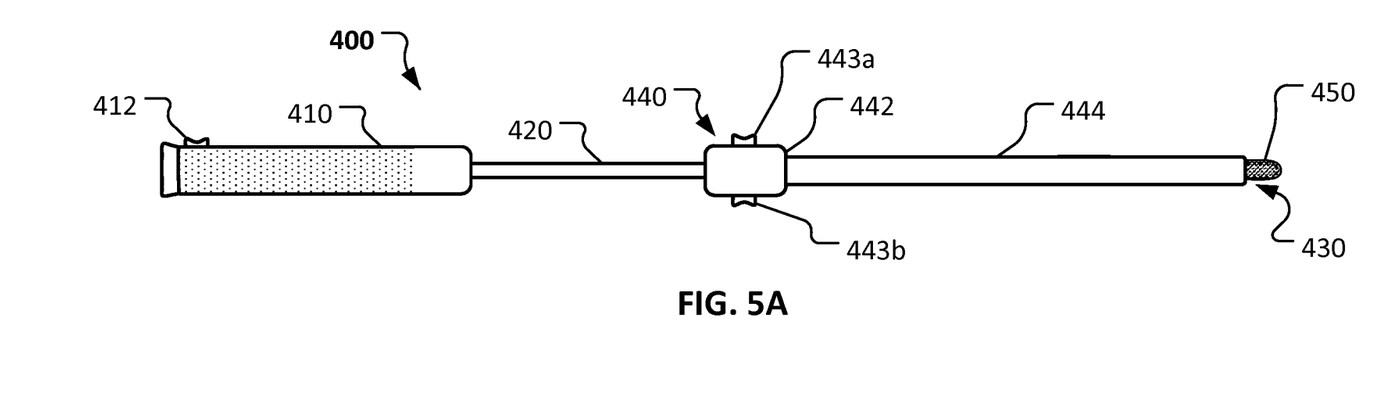
FIGS. 5A-5D show the laparoscopic retractor device of FIG. 4A in the same configurations of FIGS. 4A-4D, and with the addition of an example elastic covering on the expandable portion, in accordance with some embodiments provided herein.
Figure 5B:
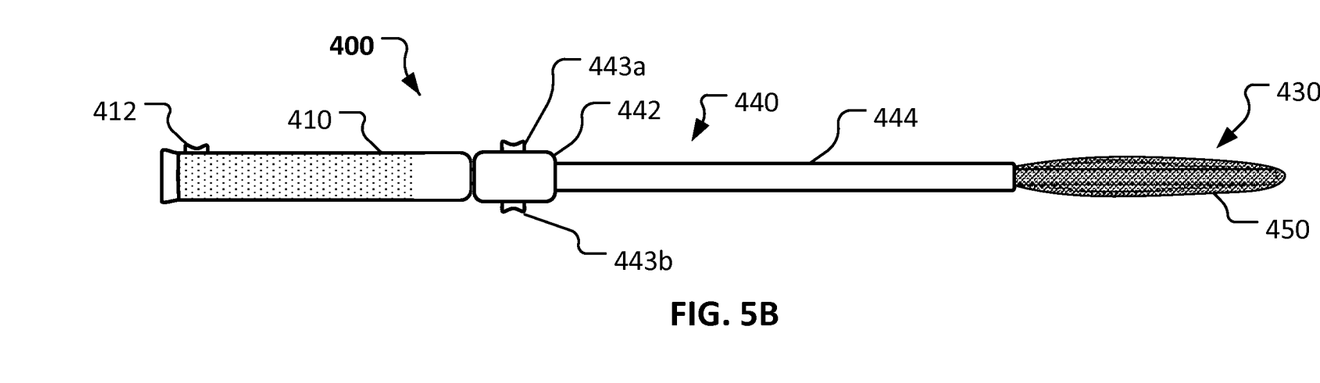
Figure 5C:
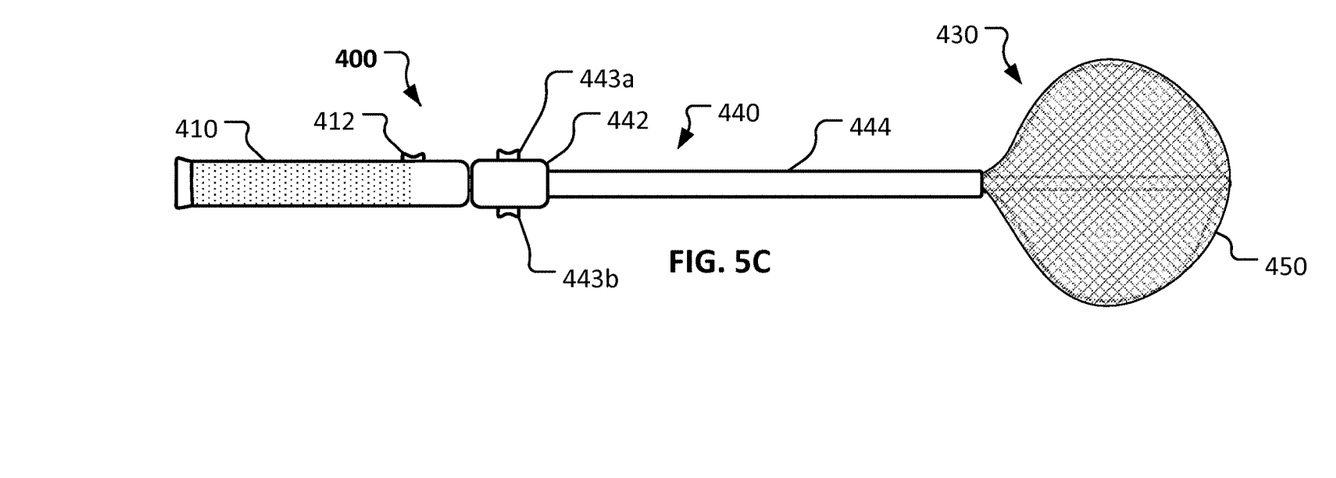
Figure 5D:
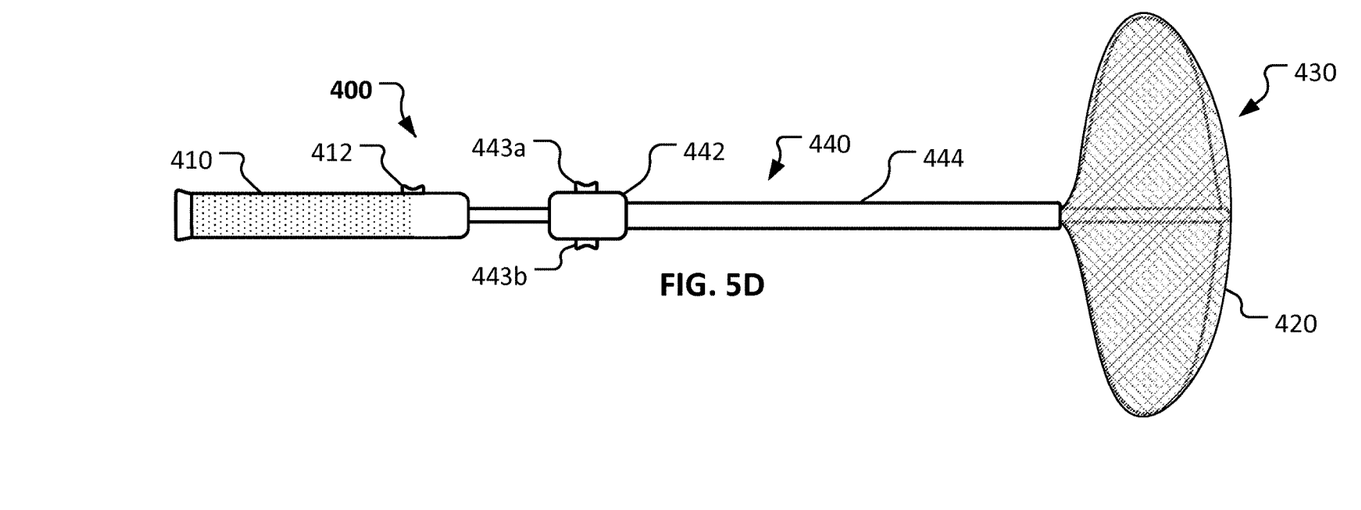

When expandable portion 430 is in the contracted configuration as shown in FIG. 5A, elastic covering 450 is also contracted such that it snugly conforms to retractor blades 432a and 432b (inside of elastic covering 450). As retractor blades 432a and 432b are expanded radially outward from shaft 420, elastic covering 450 stretches to remain surrounding and conforming to retractor blades 432a and 432b (as shown in FIGS. 5C and 5D). In some embodiments, elastic covering 450 is attached to retractor blades 432a and 432b, such as by using a biocompatible adhesive, clips, barbs, or another type of fastening means. In some embodiments, elastic covering 450 simply elastically surrounds retractor blades 432a and 432b.

Elastic covering 450 can be comprised of various materials. For example, in some embodiments elastic covering 450 can be made of materials including, but not limited to, polypropylene, natural latex, polyester, Spandex, silicone, and the like. In some embodiments, elastic covering 450 can comprise nitinol. In some embodiments, a combination of such materials can be used to make elastic covering 450. The materials used to make elastic covering 450 can be knitted, woven, spun, extruded, molded, and the like. In some embodiments, elastic covering 450 is a mesh or netting type of material. In some embodiments, elastic covering 450 is a fabric, sheet, membrane, film, or the like. In particular embodiments, elastic covering 450 can be porous or at least partially porous so as to let fluids pass through some or all portions of elastic covering 450.

Elastic covering 450 can provide functional benefits for laparoscopic retractor device 400 in some situations. For example, elastic covering 450 can enlarge the area that expandable portion 430 comprises. Accordingly, laparoscopic retractor device 400 with elastic covering 450 can provide additional retraction capabilities as compared to laparoscopic retractor device 400 without elastic covering 450, in some situations. Additionally, in some situations the use of elastic covering 450 can reduce the likelihood of pinching tissue such as bowels when laparoscopic retractor device 400 with elastic covering 450 is being expanded or retracted, as compared to laparoscopic retractor device 400 without elastic covering 450.

While this specification contains many specific implementation details, these should not be construed as limitations on the scope of any invention or of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described herein as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described herein should not be understood as requiring such separation in all embodiments, and it should be understood that the described program components and systems can generally be integrated together in a single product or packaged into multiple products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In certain implementations, multitasking and parallel processing may be advantageous.

What is claimed is:

1. A laparoscopic retractor device comprising:
    a handle;
    an elongate shaft with a proximal end portion that is attached to the handle, the shaft extending from the handle and terminating at a distal free end portion, the shaft defining a first lumen;
    an elongate shaft linkage disposed within the first lumen, the shaft linkage having a proximal end and a distal end;
    a first actuator located at the handle and coupled to the proximal end of the shaft linkage;
    an expandable portion including: (i) a distal end portion coupled to the distal free end portion of the shaft and (ii) a proximal end portion coupled to the distal end of the shaft linkage, wherein moving the actuator causes the expandable portion to move radially outward from the shaft or radially inward toward the shaft; and
    a sheath with a lumen therethrough, at least a portion of the shaft being disposed within the lumen, the sheath being slidable distally and proximally along the shaft.

2. The laparoscopic retractor device of claim 1, wherein the sheath includes a hub that is connected to a proximal end of the sheath, and wherein the hub includes a second actuator whereby the hub can be locked and unlocked from being coupled to the shaft.

3. The laparoscopic retractor device of claim 2, wherein the second actuator whereby the hub can be locked and unlocked from being coupled to the shaft is at least one of a button, an eccentric locking ring, a set screw, a thumb screw, a friction fitting arrangement, a ratchet and pawl mechanism, and a threaded arrangement.

4. The laparoscopic retractor device of claim 1, wherein the first actuator is slidable in relation to the handle.

5. The laparoscopic retractor device of claim 4, wherein sliding the first actuator distally causes the expandable portion to expand, and wherein sliding the first actuator proximally causes the expandable portion to contract.

6. The laparoscopic retractor device of claim 4, the first actuator comprising a knob, wherein the first actuator is locked into place when the knob is released.

7. The laparoscopic retractor device of claim 1, wherein the expandable portion comprises at least two retractor blades.

8. The laparoscopic retractor device of claim 7, wherein causing the expandable portion to expand comprises causing the at least two retractor blades to bend and to move radially outward from the shaft, and wherein causing the expandable portion to contract comprises causing the at least two retractor blades unbend and to move radially inward toward the shaft.

9. The laparoscopic retractor device of claim 8, wherein by sliding the sheath distally at least some portion of the at least two retractor blades can be made to move further radially away from the shaft.

10. The laparoscopic retractor device of claim 8, wherein by sliding the sheath proximally at least some portion of the at least two retractor blades can be made to move further radially inward toward the shaft.

11. The laparoscopic retractor device of claim 10, further comprising an elastic covering that is disposed around the at least two retractor blades.

12. The laparoscopic retractor device of claim 11, wherein the elastic covering is attached to the retractor blades via at least one of adhesive, clops, and barbs.

13. The laparoscopic retractor device of claim 1, further comprising an elastic covering that is disposed around the expandable portion.

14. The laparoscopic retractor device of claim 13, wherein the elastic covering is attached to the retractor blades via at least one of adhesive, clops, and barbs.

15. The laparoscopic retractor device of claim 1, wherein the first actuator is at least one of a rotary actuator, a level, and a trigger.

16. The laparoscopic retractor device of claim 1, wherein the handle comprises at least one of a textured surface and a contoured surface.

17. The laparoscopic retractor device of claim 1, wherein the shaft defines a second lumen for at least one of suction and irrigation.

* * * * *